United States Patent

Wilhoit et al.

[11] Patent Number: 6,096,420
[45] Date of Patent: Aug. 1, 2000

[54] THIN PLASTIC FILM

[75] Inventors: Darrel Loel Wilhoit, Plainfield, Ill.;
Paul Eugene Thomas, Terre Haute, Ind.

[73] Assignee: Tredegar Corporation, Richmond, Va.

[21] Appl. No.: 09/016,460

[22] Filed: Jan. 30, 1998

[51] Int. Cl.[7] ................................................. B32B 7/12
[52] U.S. Cl. ................................ 428/343; 428/355 BL; 428/356; 427/208.4
[58] Field of Search .................................. 428/343, 356, 428/355 BL; 427/208.4

[56] References Cited

U.S. PATENT DOCUMENTS

| | | | |
|---|---|---|---|
| 4,452,835 | 6/1984 | Vasudevan | 428/35 |
| 4,880,422 | 11/1989 | McBride | 604/389 |
| 5,399,177 | 3/1995 | Blaney et al. | 604/389 |
| 5,538,790 | 7/1996 | Arvedson et al. | 428/349 |
| 5,580,411 | 12/1996 | Nease et al. | 156/260 |
| 5,593,750 | 1/1997 | Rothrum et al. | 428/40.1 |
| 5,635,275 | 6/1997 | Biagioli et al. | 428/132 |
| 5,695,868 | 12/1997 | McCormack | 428/283 |
| 5,698,054 | 12/1997 | Biagioli et al. | 156/145 |
| 5,779,691 | 7/1998 | Schmitt | 428/343 X |
| 5,807,371 | 9/1998 | Toyoda et al. | 428/343 X |
| 5,853,874 | 12/1998 | Jacob | 428/343 |

FOREIGN PATENT DOCUMENTS

| | | |
|---|---|---|
| 0 407 309 A1 | 1/1991 | European Pat. Off. . |
| 52123436 | 10/1977 | Japan . |
| 06293845 | 10/1994 | Japan . |
| 06322194 | 11/1994 | Japan . |
| WO 97/47264 | 12/1997 | WIPO . |
| WO 97/47265 | 12/1997 | WIPO . |
| WO 97/47266 | 12/1997 | WIPO . |

OTHER PUBLICATIONS

Search Report, U.S. and Foreign, 33 pages.
"Holding Power of Pressure Sensitive Tape", PSTC–7, pp. 35–37, 1989.

*Primary Examiner*—Daniel Zirker
*Attorney, Agent, or Firm*—Jenkens & Gilchrist, P.C.

[57] ABSTRACT

A covering for a portion of a body or an object, as well as improved, thin plastic films for use in such coverings, are disclosed. The covering comprises a thin plastic film and a pressure sensitive adhesive contacting at least a portion of, and forming a joint with, the thin plastic film. The plastic film comprises from about 85 to about 95 weight percent plastic, and from about 5 to about 15 weight percent tackifier.

Such joints may be found in diapers, adult incontinent briefs, bandages, and other body coverings, as well as packagings for a variety of objects. Such joints exhibit unexpectedly high shear adhesion as compared to conventional joints.

54 Claims, 3 Drawing Sheets

THIN PLASTIC FILM

FIELD OF THE INVENTION

The present invention generally relates to thin plastic films and, more particularly, but not by way of limitation, to an improved joint between a thin plastic film and a pressure sensitive adhesive.

HISTORY OF THE RELATED ART

Thin plastic films are used in a variety of consumer products. Some typical applications include body coverings such as baby diapers, adult incontinent briefs, and bandages, as well as packagings for a variety of other products. In each of these applications, a joint between the thin plastic film and a pressure sensitive adhesive may be required.

FIGS. 1 and 2 show schematic views of a conventional diaper 10. Referring first to FIG. 1, diaper 10 has a backsheet 12 formed from a thin plastic film. Backsheet 12 is formed into a "T-shape" so that tee extensions or tee tabs 14 can be used like a belt or strap for fastening diaper 10 around a baby. A landing zone 16 is located on the opposite end of backsheet 12 from tee tabs 14. Diaper tapes 17 are adhered to backsheet 12 at each end of tee tabs 14.

FIG. 2 shows a detailed view of the coupling of diaper tapes 17 to backsheet 12. Each diaper tape 17 preferably includes a tape substrate 18, a pressure sensitive adhesive 20 coated to one surface of tape substrate 18, and a release paper 22 coupled to the outwardly extending end of each substrate 18 so as to cover pressure sensitive adhesive 20. Joints 24 between backsheet 12 and pressure sensitive adhesive 20 couple diaper tapes 17 to backsheet 12. Joints 24 are non-refastenable joints. In other words, the removal of diaper tape 17 from backsheet 12 destroys diaper tape 17, backsheet 12, or both.

As also shown in FIG. 2, diaper 10 includes an absorbent core 26 and a topsheet 28, which is typically formed from a nonwoven polymeric fiber or film. Top sheet 28 contacts a baby's skin. When diaper 10 is initially placed on a baby, tee tabs 14 extend along the baby's back, and diaper 10 is placed through the baby's crotch so as to position landing zone 16 near the baby's stomach. Tee tabs 14 are then used to encircle the baby's waist. Release papers 22 are removed from diaper tapes 17 and discarded, and diaper tapes 17 are affixed to landing zone 16 so as to secure diaper 10 on the baby. When diaper tapes 17 are affixed to landing zone 16, they are subjected to a continuing tensile stress. This tensile stress creates a shear field in joints 24. Since diaper 10 may remain on a baby for as long as twelve to fourteen hours (720 to 840 minutes) at body temperature, joints 24 must be able to withstand these conditions.

FIG. 3A shows a schematic view of a conventional bandage 50. Bandage 50 generally includes a thin plastic film 52, a pressure sensitive adhesive 54 coated on one surface of film 52, and a bandage pad 56. Thin plastic film 52 is typically formed with apertures or holes therethrough to allow a user's skin to breath. Pressure sensitive adhesive 54 bonds pad 56 to film 52. As shown in FIG. 3B, bandage 50 may be wrapped around a user's finger or other appendage 55 so that pressure sensitive adhesive 54 forms a lap joint 57 on a top surface 58 of bandage 50. When applied to a user's finger in the manner shown in FIG. 3B, film 52 is subjected to a continuing tensile stress that creates a shear field in joint 57. Since bandage 50 may remain on a user's skin for as long as several days at body temperature, joint 57 must be able to withstand these conditions.

FIG. 4 shows a schematic of a thin plastic film 70 used as a packaging for a object 72. Film 70 is not a "cling film", meaning that it does not have a tendency to stick to itself, or stick to itself after being stretched around object 72. Instead, film 70 is formed around, and is generally sealed to enclose, object 72. A label 74 is often attached to a surface of film 70 to identify, or otherwise describe, object 72. A pressure sensitive adhesive 76 is coated to the rear side of label 74 and is used to form a joint 78 between label 74 and plastic film 70. In addition, plastic film 70 is often embossed, or otherwise formed, with a pattern on its exterior surface for aesthetic purposes.

Backsheet 12, thin plastic film 52, and thin plastic film 70 are thermoplastic films, and they are most typically thermoplastic films comprising a polyolefin or blend of polyolefins. Pressure sensitive adhesives 20, 54, and 76 are typically rubbery polymers, and they are most typically rubbery polymers containing a tackifier. For example, one conventional pressure sensitive adhesive, which has been used as pressure sensitive adhesive 20 for diaper tapes 17 of diaper 10, comprises about 40 weight percent styrene-isoprene-styrene block copolymer, about 40 weight percent hydrocarbon resin tackifier, and about 20 weight percent low molecular weight plasticizing oil.

The above-described plastic films and pressure sensitive adhesives have achieved some success in forming strong joints in many consumer products, such as joints 24 with backsheet 12 in diaper 10; joint 57 with top surface 58 of bandage 50; and joint 78 with plastic film 70. However, these joints are subject to certain limitations. For example, when the plastic films, and/or the joints formed between the plastic films and the pressure sensitive adhesives, are subjected to high ambient temperature conditions for an extended period of time, such as during storage in a warehouse in a hot climate, the strength of such joints is adversely affected. In addition, when such plastic films are formed with a rough surface, such as, by way of example, embossing a large scale pattern on the film, or forming apertures or holes in the film, the strength of a joint formed using such film is adversely affected. Furthermore, when such joints are subjected to moisture, such as when a person washes a portion of their body onto which bandage 50 has been applied, a stronger joint is needed to withstand such conditions.

Several conventional techniques have been employed in an attempt to combat these limitations. First, the composition of the pressure sensitive adhesive may be altered to increase the strength of the adhesive, and thus the joint. However, it is often difficult to find, or cost-prohibitive to use, a commercially available pressure sensitive adhesive that has the necessary adhesive properties to form such joints. Furthermore, higher strength adhesives may not be applicable in bandage 50 where the adhesive contacts the user's skin. Still further, in the case of diaper tapes 17 of diaper 10, although increasing the strength of pressure sensitive adhesive 20 will form a stronger joint 24 with backsheet 12, it will also cause the joint between pressure sensitive adhesive 20 and landing zone 16 to be non-refastenable. This joint is preferably refastenable so as to minimize waste of diapers 10.

It is also known to treat the plastic film by various means to enhance the affinity of the film surface to the pressure sensitive adhesive. Corona treatment is an example of one such technique. However, the beneficial surface activation achieved by corona treatment decreases quickly with time at high ambient temperatures. Other techniques include plasma treatment, flame treatment, ozone treatment, and chemical etching. However, these techniques require expensive and physically large equipment and involve dangerous substances or sources of combustion.

Therefore, a need exits in the plastic film industry for an improved plastic film capable of forming a strong joint with a pressure sensitive adhesive, and which overcomes, or minimizes, the above-described limitations of conventional films.

SUMMARY OF THE INVENTION

The present invention comprises a covering for a portion of a body or an object, as well as improved, thin plastic films for use in such coverings. The covering comprises a thin plastic film and a pressure sensitive adhesive contacting at least a portion of, and forming a joint with, the thin plastic film. The plastic film comprises from about 85 to about 95 weight percent plastic, and from about 5 to about 15 weight percent tackifier.

The covering may be a diaper having a diaper tape coated with the pressure sensitive adhesive. In this case, the thin plastic film is a diaper backsheet, and the pressure sensitive adhesive couples the diaper tape to the diaper backsheet to form a non-refastenable joint.

The covering may alternatively be a bandage. In this case, the thin plastic film is the bandage.

The covering, and the thin plastic film, may alternatively be a packaging for an object. In this case, the present invention further comprises a label, and the pressure sensitive adhesive couples the label to the packaging.

The covering may alternatively be an incontinent brief, a medical drape, a medical gown, a medical smock, an ostomy appliance, a feminine hygiene product, a body transfer sheet, a fluid collection pouch, or an industrial clean room garment.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1–6 of the drawings, like numerals being used for like and corresponding parts of the various drawings. The following abbreviations are utilized in the description hereinbelow: CAS—Chemical Abstract; COF—coefficient of friction; $MW_w$—weight average molecular weight; EMAC—ethylene methacrylate; EVA—ethyl vinyl acetate; HDPE—high density polyethylene; LDPE—low density polyethylene; LLDPE—linear low density polyethylene; LMDPE—linear medium density polyethylene; ULDPE—ultra low density polyethylene; mPOE—metallocine polyolefin elastomer; PP—polypropylene; iso PP—isotatic polypropylene; FPO—flexible polyolefin resin sold by the Huntsman Polymer Corporation of Odessa, Tex.; MI—melt index (grams/10 minutes @ 190° C.); SHT—shear hang time; HASHT—high ambient shear hang time.

Figure 1:
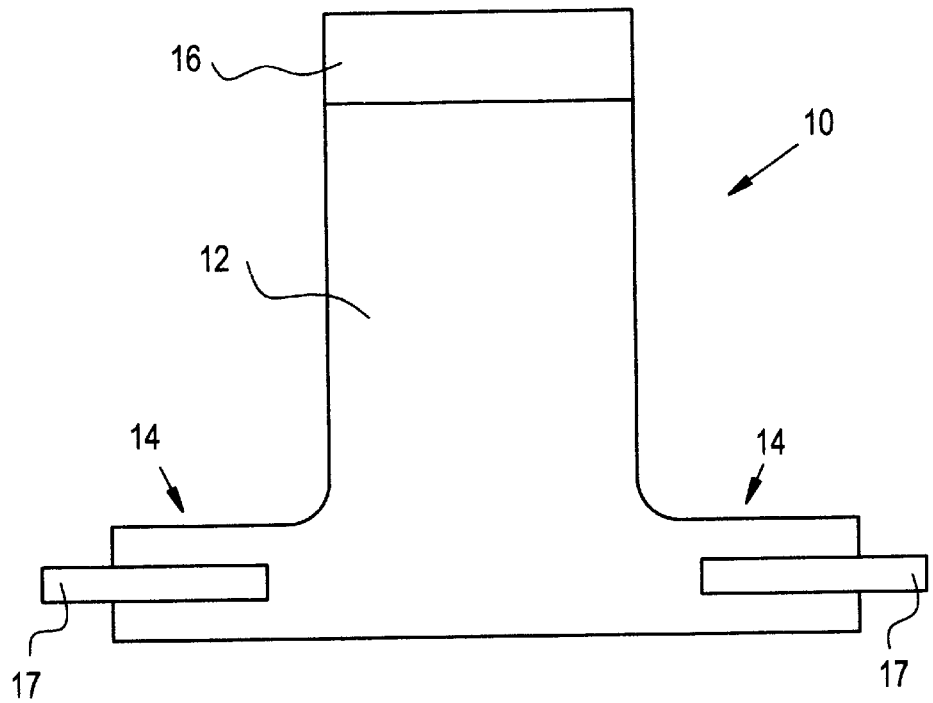
FIG. 1 is a schematic, bottom view of a conventional diaper 10.
Figure 2:
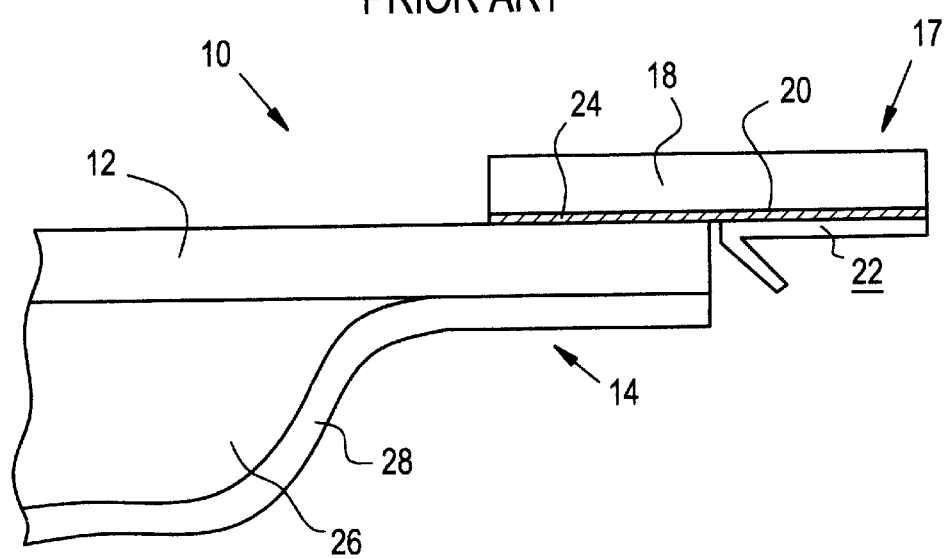
FIG. 2 is an enlarged, fragmentary, cross-sectional view of the diaper of FIG. 1 showing the coupling of the diaper tapes to the diaper backsheet.
Figure 3A:
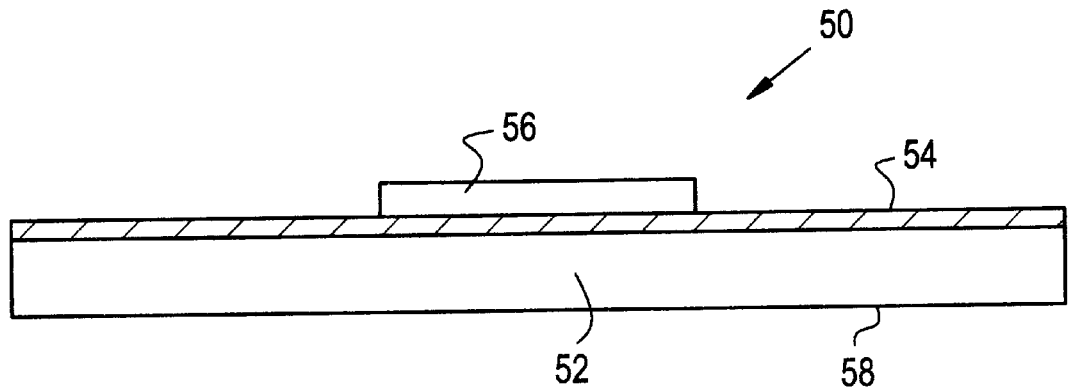
FIG. 3A is a schematic, side elevational view of a conventional bandage.
Figure 3B:
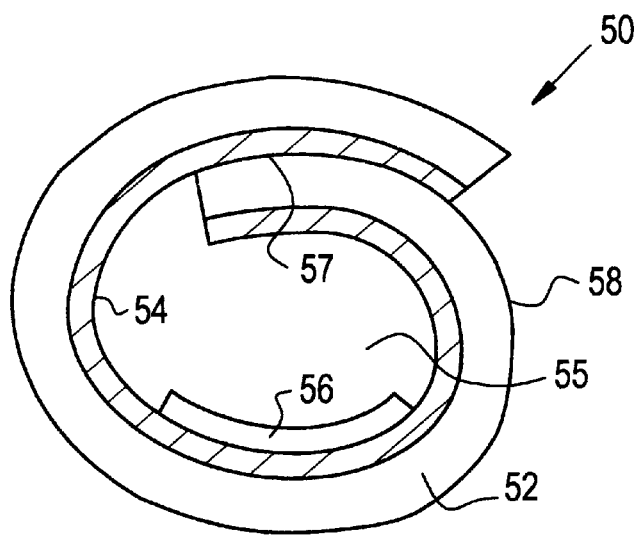
FIG. 3B is a schematic, top cross-sectional view of the bandage of FIG. 3A wrapped around a user's finger.
Figure 4:
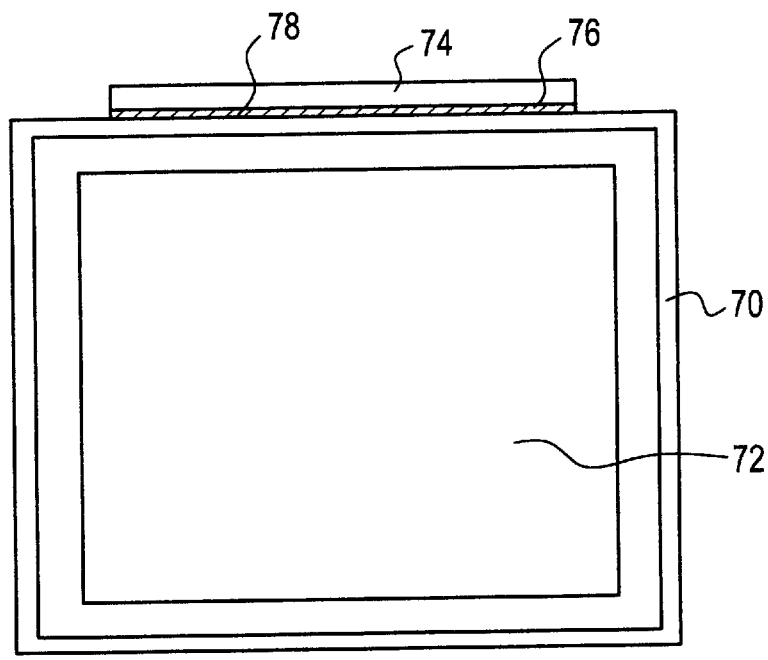
FIG. 4 is a schematic, cross-sectional view of a thin plastic film used as packaging for a object with a conventional pressure sensitive adhesive label attached to a surface of the film.
Figure 5:
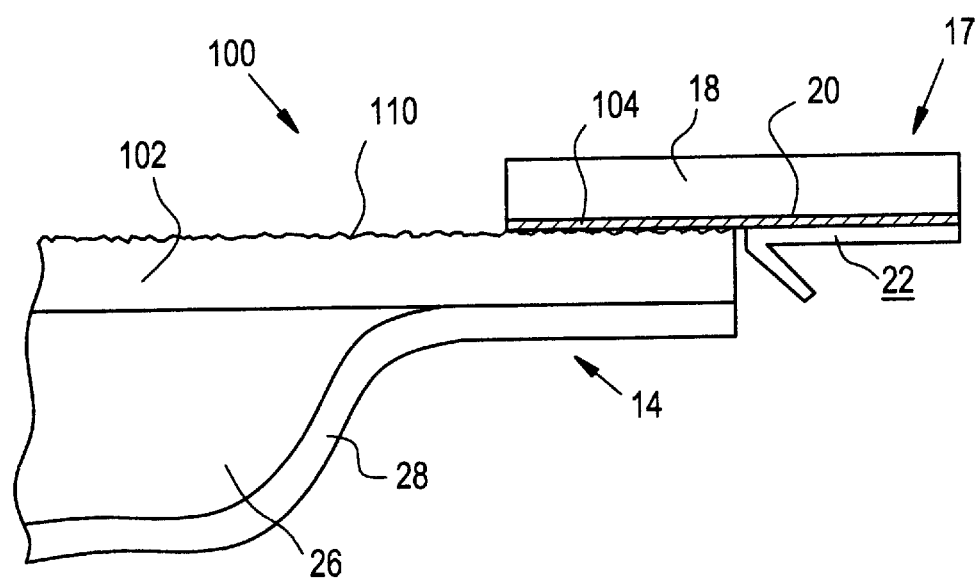
FIG. 5 is fragmentary, cross-sectional view of a diaper showing a coupling of the diaper tapes to a diaper backsheet having a large scale, rough surface according to a preferred embodiment of the present invention.

Referring first to FIG. 5, a coupling of diaper tapes 17 to a backsheet 102 of a diaper 100 is shown according to a preferred embodiment of the present invention. Diaper 100 preferably has a similar geometry to the geometry of diaper 10 as shown in FIG. 1. Joints 104 between backsheet 102 and pressure sensitive adhesive 20 couple diaper tapes 17 to backsheet 102. Diaper 100 includes an absorbent core 26 and a topsheet 28, which is preferably formed from a nonwoven polymeric fiber or film. Backsheet 102 differs from backsheet 12 of FIGS. 1 and 2 only in that it has been formed with a large scale, rough surface 110. As used in this document, the term "large scale, rough surface" means a surface formed with from about a 40 mesh to about an 80 mesh pattern, or a similarly rough surface. Such a surface is representative of large scale embossing. An 80 mesh pattern has about 6,400 protuberances per square inch. Large scale, rough surfaces are desirable on diaper backsheets to decrease the gloss of the film surface, to decrease the stiffness of the backsheet, to decrease noise and rattle of the backsheet, to make the backsheet feel more cloth-like, and to generally improve the aesthetic properties of the backsheet. One will appreciate that a bandage similar to bandage 50 of FIGS. 3A and 3B may also be formed with a surface 58 that is a large scale, rough surface, and that a thin plastic film similar to plastic film 70 of FIG. 4 may also be formed with a large scale, rough surface, if desired.

A shear adhesion test that follows the Pressure Sensitive Tape Council Procedure Number 7 (Revised August 1989) (hereinafter "PSTC-7"), and more particularly follows the procedure disclosed in U.S. Pat. No. 5,399,177, has been used to simulate the shear stress imposed on joints between thin plastic films and pressure sensitive tapes, such as joints 24 with backsheet 12 in diaper 10, joint 57 in bandage 50, joint 78 with plastic film 70, and joint 104 with backsheet 102 in diaper 100. PSTC-7 and U.S. Pat. No. 5,399,177 are incorporated herein by reference in their entirety. Although applicable to all these applications, this test is described hereinbelow with reference to diaper 10 for convenience of illustration.

A portion of diaper tape 17 is coupled to a portion of backsheet 12 via pressure sensitive adhesive 20. Diaper tape 17 is suspended from a clamp on its free end, and a one kilogram weight is attached to the portion of backsheet 12. This sample is held at 100° F. (approximately body temperature) until backsheet 12 slides away from pressure sensitive adhesive 20 of diaper tape 17. Failure almost always occurs in a creep mode. This test is referred to as a shear hang time (SHT) test, and its units are in minutes to failure. For diaper 10, a desired SHT is about 500 minutes, and is more preferably about 1000 minutes or higher.

PSTC-7 and U.S. Pat. No. 5,399,177 allude to SHT testing done at elevated temperatures, such as in the range of 100° F. to 120° F. Such elevated temperature SHT testing is of particular importance to the characterization of the performance of joints such as joints 24, 57, 78, and 104. As described hereinabove, finished products having such joints are often stored in high ambient temperature warehouse environments. Therefore, a variation on the SHT test procedure to include high ambient temperature environments has also been used. In this document, this variation is referred to as the high ambient shear hang time (HASHT) test.

In the HASHT test, a portion of diaper tape 17 is coupled to a portion of backsheet 12 via pressure sensitive adhesive 20, and this sample is stored at 120° F. for three days. The aged sample is then subjected to the above-described SHT test procedure. High ambient shear hang times are always lower than shear hang times, with high ambient shear hang times typically being from about 7 to about 55 percent lower than corresponding shear hang times for a given joint. However, the desired HASHT is still about 500 minutes, and is more preferably about 1000 minutes or higher. It is believed that high ambient temperatures encourage the migration of the low molecular weight components to the surface of both backsheet 12 and pressure sensitive adhesive 20, weakening joint 24. The 120° F. exposure of joint 24 is carried out for three days because it is believed that most of the damaging migration takes place in that time frame.

An exemplary thin plastic film conventionally used as backsheet 12, and an exemplary pressure sensitive adhesive conventionally used as pressure sensitive adhesive 20 for diaper tapes 17, were used as controls for demonstrating the HASHT performance of joints formed between thin plastic films and pressure sensitive adhesives. The composition of the control film, by weight percent, was 45%. Dow 2247A (LLDPE), 20% Dow KC8852 (mPOE), 20% Westlake EF378AA (LDPE), 5% Southwest 1071 (66% $TiO_2$, 33% LDPE), and 10% Amoco 6345 (iso PP). The composition of the control pressure sensitive adhesive was about 40 weight percent styrene-isoprene-styrene block copolymer, about 40 weight percent hydrocarbon resin tackifier, and about 20 weight percent low molecular weight plasticizing oil. The control film was coupled to a diaper tape 17 having a tape substrate 18 coated with the control pressure sensitive adhesive.

The control film was made as a monolayer film on a laboratory scale Killion extruder, and was formed with several different surface patterns. First, the control film was formed with a smooth surface, similar to backsheet 12 of diaper 10. Second, the control film was formed with a fine scale, rough surface, such as about 170 mesh or finer. Third, the control film was formed with a large scale, rough surface, similar to surface 110 of backsheet 102 of diaper 100.

When the control films formed with a smooth surface and a fine scale, rough surface were subjected to the HASHT test, the samples did not fail. However, when the control film formed with a large scale rough surface was subjected to the HASHT test, the sample failed after about 60 minutes, substantially below the desired HASHT of about 500 minutes. Stated more generally, it has been determined that conventional thin plastic films and pressure sensitive adhesives form acceptably strong joints when the films are smooth or finely textured. However, when the films have a large scale, rough surface, and particularly when such joints are subjected to high ambient temperatures, such as 120° F., for several days, the joints fail under shear in an unacceptably short time frame.

However, joints formed between the improved plastic films of the present invention having a large scale, rough surface and the control pressure sensitive adhesive exhibited a HASHT from about 2 to about 138 times that of joints formed with the control film having a large scale, rough surface and the control pressure sensitive adhesive. This significant increase in shear adhesion is unexpectedly obtained by modifying the composition of the thin plastic film, rather than modifying the composition of the pressure sensitive adhesive, or treating the film subsequent to its formation to enhance its affinity to the pressure sensitive adhesive. More specifically, the improved plastic films of the present invention contain a tackifier in the amount of about 5 to about 15 weight percent. In addition, the improved plastic films of the present invention preferably also contain a flexible, or rigid, polypropylene in the amount of about 7 to about 15 weight percent. Although tackifiers are typically used in the formation of adhesives, the improved films are not sticky to the touch, and the improved films do not block, or adhere to themselves, when they are wound into rolls. In addition, joints formed using the improved films exhibit greater shear adhesion, as measured by HASHT, than conventional joints when the film itself is exposed to high temperatures for an extended period of time before being made into a joint.

It is believed that the tackifiers of the improved films increase the affinity of the plastic film to the pressure sensitive adhesive by improving the surface wettability of the film and increasing the interfacial bond strength between the film surface and the adhesive. The improved films of the present invention can be used to form joints 24, joint 57, joint 78, joints 104, or other similar joints.

The thin plastic films of the present invention preferably comprise from about 85 to about 95 weight percent plastic, and from about 5 to about 15 weight percent tackifier. More preferably, the thin plastic films of the present invention comprise from about 90 to about 95 weight percent plastic, and from about 5 to about 10 percent weight percent tackifier. In addition, the thin plastic films of the present invention may contain from about 1 to about 5 weight percent of an opaquing agent, coloring agent, or similar pigment, as a substitute for a like amount of plastic. A preferred opaquing agent is $TiO_2$.

The plastic, or polymeric, component may comprise a plastic, or a blend of plastics. The plastic, or blend of plastics, may comprise polyolefins, polyesters, polyvinyl florides, polyamides, polyvinyl chlorides, acrylics, acetals, polycarbonates, polystyrenes, polyurethanes, and copolymeric and terpolymeric variations of these plastics.

In a first embodiment, the plastic component preferably comprises a polyolefin or a blend of polyolefins. Still more preferably, the plastic component is a blend of polyethylene, LDPE, LLDPE, LMDPE, HDPE, ULDPE, mPOE, EMAC, and/or polypropylene, including selected combinations of the above. Still more preferably, the plastic component is a blend of polyethylene, mPOE, and polypropylene, or a blend of polyethylene, EMAC, and polypropylene. In this embodiment, the tackifier preferably comprises a hydrocarbon resin or a blend of hydrocarbon resins. For example, the tackifier may comprise an aliphatic resin, a copolymer of aliphatic resins, a hydrogenated or partially hydrogenated compound of aliphatic resins, or a blend of aliphatic resins. As another example, the tackifier may comprise an aromatic resin, a copolymer of aromatic resins, a hydrogenated or partially hydrogenated compound of aromatic resins, or a blend of aromatic resins. Alternatively, the tackifier may comprise a non-hydrocarbon resin such as a coumarone-indene resin, a polyterpene resin, or a resin derived from plant by-products.

As described hereinabove, joints may be formed between the improved plastic films of the present invention and commercially available pressure sensitive adhesives typically used in conjunction with a tape substrate. Preferably such pressure sensitive adhesives are rubbery polymers. More preferably, such pressure sensitive adhesives are rubbery polymers containing a tackifier. Still more preferably, such pressure sensitive adhesives are rubbery polymers containing a hydrocarbon resin tackifier. A specific preferred pressure sensitive adhesive, especially for diaper applications, is the control pressure sensitive adhesive. However, the present invention is believed to be fully applicable with other pressure sensitive adhesives containing rubbery polymers such as styrene-butadiene-styrene block copolymers, natural rubber, atatic polypropylenes, POEs, and EVAs. To maximize the strength of joints formed with any of these pressure sensitive adhesives, a tackifier having a specific affinity for the rubbery component of the pressure sensitive adhesive is added to the plastic film. Of course, the specific tackifier, and the amount thereof, added to the plastic film will require optimization.

In a second embodiment that is believed to be particularly useful in bandages such as bandage 50, the plastic component preferably comprises a blend of a mPOE and an EVA having a ratio by weight of about 3 to 1, respectively. In this embodiment, a tackifier having a high affinity for a rubbery component of a pressure sensitive adhesive and that is readily melt dispersible in the mPOE and EVA blend is utilized.

In both the first and second embodiments described above, the thin plastic film of the present invention is preferably formed in the following manner. First, a pure, or neat, tackifier is melt blended with a polymer diluent to form a tackifier concentrate. These tackifier concentrates are formed because most pure tackifiers melt prematurely on the extruder screw of conventional film extruders due to their low melting point. When tackifier accumulates on the upstream flights of the extruder screw, it ceases to function normally. To avoid the problem of screw fouling caused by using the pure tackifier in the dry blend of the film formulation, the tackifier is preferably melt blended with a suitable polymer diluent, such as polyethylene or polypropylene, in a separate previous step. A conventional twin screw extruder can be used to melt blend the pure tackifier and polymer diluent. Second, the desired amounts of tackifier concentrate and the other plastic components are dry blended using conventional blending equipment, and the resulting dry blend is passed into the main feed hopper of a conventional film extruder. Third, the dry blend is extruded under temperature and pressure in the film extruder and passed through a die to form a thin plastic film. The film extruder preferably has a mixing section to insure uniform distribution of components within the thin plastic film. Alternatively, the plastic components, less the tackifier or tackifier concentrate, may be dry blended and passed into the main feed hopper of the film extruder. At a point downstream in the film extruder barrel, pure tackifier may be injected as a molten liquid, eliminating the need for having to make and use a tackifier concentrate.

TABLE I

| | | Tackifiers | | | | | Improved Films (1) | | |
|---|---|---|---|---|---|---|---|---|---|
| Tackifier | Manufac. | R & B Softening (2) (° C.) | MMAP (3) (° C.) | MWw | Resin Type | CAS No. | Example | Ratio HASHT to control (4) | Film Composition |
| Regal Rez 1139 | Hercules | 140 | 108 | 3100 | Hydrogenated Styrene | 68441-38-3 | 1 | 8.6 | (7) |
| Regallite R91 | Hercules | 88 | 74 | 700 | Hydrogenated Aliphatic/Aromatic Copolymer | proprietary | 2 | 9.3 | (8) |
| Hercotac 1149 | Hercules | 98 | 68 | 1850 | Aliphatic/Aromatic | proprietary | 3 | — | (5), (12) |
| Wingtac 95 | Goodyear | 95 | ~95 | 1300 | Aliphatic piperylenes | 28613-14-9 | 4 | 39.3 | (8) |
| Picotac 95 | Hercules | 95 | 95 | 1360 | Aliphatic piperylenes | 152698-66-3 | 5 | — | (5), (9) |
| LX509 | Neville | — | — | — | Coumarone-Indene | 6683-19-8 | 6 | 17.1 | (8) |
| Zonarez 71-15 | Arizona | — | — | — | Terpene | proprietary | 7 | 31.4 | (8) |
| Zonatac 105 | Arizona | 105 | — | — | Styrenated Terpene | proprietary | 8 | 17.1 | (8) |
| Arcon P125 | Arakawa | 125 | — | — | Alicyclic | 68132-35-3 | 9 | 25.7 | (8) |
| Krystalex 3100 | Hercules | 100 | 4 | 1600 | Methyl Styrene | 9011-11-4 | 10 | 27.7 | (9) |
| Kystalex 5140 | Hercules | 140 | 9 | 4800 | Methyl Styrene | 9011-11-4 | 11 | 135 | (9) |
| Regal Rez 3102 | Hercules | — | 24 | 1300 | Partially Hydrogenated Styrene | 68441-37-2 | 12 | 40 | (9) |
| Regal Rez 6108 | Hercules | — | 54 | 1500 | Partially Hydrogenated | 68441-37-2 | 13 | 87 | (9) |
| Regal Rez P2594 | Hercules | 139 | 60 | 800 | Hydrogenated Hydrocarbon | proprietary | 14 | 49 | (10) |
| Wingtac 95 | Goodyear | 95 | ~95 | 1300 | Aliphatic piperylenes | 26813-14-9 | 15 | — | (5), (6) |
| Wingtac 95 | Goodyear | 95 | ~95 | 1300 | Aliphatic piperylenes | 26813-14-9 | 16 | 33 | (11) |

Notes:
1. All control and improved films are monolayer films made on Killion extruder and embossed with a 40–80 mesh male pattern on surface. All compositions are weight percent.
2. Ring and Ball Softening Temperature
3. MMAP is the temperature at which cloudiness in an aniline solution occurs. The higher the temperature, the greater the solubility in polyethylene.
4. Ratio of HASHT value for improved film vs. control film. (Higher is better)
5. Not run on Killion Extruder.
6. 32% Dow 2035 (LLDPE), 17% Eastman 964F (LDPE), 20% Dow KC8852 (mPOE), 3% Southwest 1071 (66% TiO$_2$, 33% LDPE), 8% Amoco 6345 (iso PP), 20% tackifier concentrate (50%–50% melt blend of tackifier and LDPE (2M1)).
7. 36.7% Dow 2035 (LLDPE), 13% Chevron 2260 (EMAC), 16.3% Chevron 2121 (LDPE), 3% Southwest 1071 (66% TiO$_2$, 33% LDPE), 18% tackifier concentrate (50%–50% melt blend of tackifier and PP), 13% Rexene W102 (FPO PP)
8. 36.7% Dow 2035 (LLDPE), 13% Chevron 2260 (EMAC), 16.3% Chevron 2121 (LDPE), 3% Southwest 1071 (66% TiO$_2$, 33% LDPE), 18% tackifier concentrate (50%–50% melt blend of tackifier and Chevron 2121 (LDPE)), 13% Rexene W102 (FPO PP)
9. 32% Dow 2035 (LLDPE), 20% Dow KC8852 (mPOE), 19.2% Chevron 2121 (LDPE), 3% Southwest 1071 (66% TiO$_2$m 33% LDPE), 13% Rexene Wl02 (FPO PP), 20% tackifier concentrate (50%–50% melt blend of tackifier and LDPE (2M1, barefoot))
10. 32% Dow 2035 (LLDPE), 20% Dow KC8852 (mPOE), 19.2% Chevron 2121 (LDPE), 3% Southwest 1071 (66% TiO$_2$, 33% LDPE), 32% Rexene Wl02 (FPO PP), 12.8% Hercules Regal Rez P2594 (tackifier concentrate)
11. 24% Dow 2035 (LLDPE), 20% Dow KC5852 (mPOE), 3% Southwest 1071 (66% TiO$_2$, 33% LDPE), 13% Rexene Wl02 (FPO PP), 40% tackifier concentrate (25% tackifier, 75% LDPE (2 MI, barefoot) melt blend)
12. 32% Dow 2035 (LLDPE), 20% Dow KC8852 (mPOE), 12% Chevron 2121 (LDPE), 3% Southwest 1071 (66% TiO$_2$m 33% LDPE), 13% Rexene W102 (FPO PP), 20% tackifier concentrate (50%–50% melt blend of tackifier and LDPE (1.3 MI, barefoot))

In Table 1, above, the results of a testing process used to identify preferred tackifiers for the improved plastic films of the present invention, and preferred examples of the improved plastic films of the present invention, are shown. The left hand side of Table 1 identifies the preferred tackifiers by name, manufacturer, resin type, and CAS number, when available. The CAS numbers listed in FIG. 6 each refer to a particular CAS Registry Copyright, and each of these CAS Registry Copyrights is incorporated herein by reference. In addition, properties such as Ring and Ball Softening Temperature, MMAP, and MW$_w$ are also shown for each tackifier, where available. The MMAP and $MW_w$ are generally indicative of the solubility and compatibility of the tackifiers in polyethylene. In polyethylene, such solubility and compatibility are most favorable when the MMAP is relatively high, such as between about 60° C. to about 90° C., and when the $MW_w$ is relatively low, such as between about 1000 to about 3000. However, MMAPs between about 4° C. to about 110° C., and $MW_w$ between about 500 to about 5000, are believed to be acceptable in certain plastic films in which polyolefins are not the predominant polymer type.

The right hand side of Table 1 shows sixteen preferred examples of the improved plastic films of the present invention, as well as the ratio of HASHT for each improved film to the HASHT for the control film. Each exemplary improved film, and the control film, were made into monolayer films on a laboratory scale Killion extruder and embossed with a 40–80 mesh male pattern. As described hereinabove, a 40–80 mesh male pattern is representative of a large scale, rough surface or large scale embossing. The exact composition of each of the exemplary improved films, including the tackifier concentrates, is detailed in the footnotes of Table 1. All HASHT data in FIG. 6 was measured using a tape coated with the control pressure sensitive adhesive. Of course, the higher the HASHT ratio, the better the improved film performed in forming joints with the control pressure sensitive adhesive.

For reasons of elastic performance and improved resistance to exposure to high ambient temperatures, such as in the HASHT test, some of the tackifiers in Table 1 are preferred to others. However, all of the tackifiers and exemplary films in Table 1 are beneficial in applications involving exposure to high ambient temperatures.

Wingtac 95, Picotac 95, Regal Rez 6108, and Regal Rez P2594 yield films with good elasticity and very good HASHT performance when formed with a large scale, rough surface. Therefore, these tackifiers, or other tackifiers with similar compositions and performance properties, are preferred for diaper and bandage applications. Wingtac 95 and Picotac 95 are each polymers or copolymers of 2-methyl-2-butene-piperylene. Regal Rez 6108 is a partially hydrogenated polymer or copolymer of 1-methylethenyl benzene.

Regal Rez 1139, Regallite R91, Hercotac 1149, Neville LX509, Zonarez 71-15, Zonatac 105, Arcon P125, Krystalex 3100, Krystalex 5140, and Regal Rez 3102 all yield films with desirable HASHT performance when formed with a large scale, rough surface. Therefore, these tackifiers, or tackifiers with similar compositions and performance properties, are preferred for pressure sensitive label or similar applications that do not require diaper-specific or bandage-specific performance criteria. Regal Rez 1139 is a hydrogenated polymer or copolymer of 1-methylethenyl benzene. Regal Rez 3102 is a partially hydrogenated polymer or copolymer of 1-methylethenyl benzene. Krystalex 3100 and 5140 are each polymers or copolymers of methylstyrene-styrene.

As mentioned hereinabove, the improved films listed in Table 1 were formed with a 40–80 mesh surface pattern. A given film will exhibit a lower HASHT when formed with a 40 mesh surface pattern than when formed with an 80 mesh surface pattern. Adhesion to a 40 mesh pattern is poorer than to an 80 mesh pattern because the surface area available for bonding on the 40 mesh pattern is coarser. However, it is believed that the absolute value of HASHT for each of the exemplary films in Table 1, when formed with an 80 mesh surface pattern, is at least 500 minutes, and many are greater than 1000 minutes.

As shown in Table 1, many of the preferred examples of improved films contain $TiO_2$, a conventional opaquing agent. Of course, if an opaque film is not desired, the weight percent of $TiO_2$ for a given exemplary film may be eliminated and replaced with an equivalent weight percent of 50% LLDPE and 50% LDPE. In addition, it is believed that each of the preferred, exemplary films exhibit no significant tendency to block. Blocking is the tendency of a film to adhere to itself when it is wound into a roll. For example, tests were run to measure the blocking forces, as determined by ASTM D 3354-89 "Standard Test Method for Blocking Load of Plastic Film by the Parallel Plate Method", for the control film and Example 16 of FIG. 6. The control film, with a blocking force of about 0.20 $g/cm^2$, exhibited no significant tendency to block. Example 16, with a blocking force of about 0.47 $g/cm^2$, also exhibited no significant tendency to block.

All of the preferred, exemplary films listed in Table 1 contain a flexible polypropylene (FPO PP), with the exception of Example 15, which contains a rigid polypropylene (iso PP). Example 15 thus illustrates that either flexible or rigid polypropylene may be satisfactorily used in the improved films of the present invention.

From the above, it will be appreciated that, as compared to conventional thin plastic films, the improved plastic films of the present invention may be used to form joints with conventional pressure sensitive adhesives that exhibit unexpectedly strong performance when the film has a rough surface or when the film is exposed to high ambient temperatures for an extended period of time. In addition, the improved films of the present invention are not "sticky" to the touch and exhibit no significant tendency to block. Still further, the improved films of the present invention are economical and safe to manufacture.

The present invention is illustrated herein by example, and various modifications may be made by a person of ordinary skill in the art. For example, numerous geometries, including the above-described geometries of the joints formed between the improved films of the present invention and a pressure sensitive adhesive, could be altered. As another example, although the present invention has been described in connection with baby diapers, incontinent briefs, bandages, and applying pressure sensitive adhesive labels to plastic film packagings, the improved films of the present invention are fully applicable to other, similar products, including, without limitation, other body coverings where a pressure sensitive adhesive joint with a plastic film is contemplated. Such body coverings may include medical drapes, medical gowns, medical smocks, ostomy appliances, feminine hygiene products, body transfer sheets, fluid collection pouches, or industrial clean room garments.

It is thus believed that the operation and construction of the present invention will be apparent from the foregoing description. While the apparatus and compositions shown or described have been characterized as being preferred it will be obvious that various changes and modifications may be made therein without departing from the spirit and scope of the invention as defined in the following claims.

What is claimed is:

1. A covering for a portion of a body or an object, comprising:

a thin plastic film, said plastic film comprising from about 85 to about 95 weight percent plastic, and from about 5 to about 15 weight percent tackifier; and a pressure sensitive adhesive contacting at least a portion of, and forming a joint with, said thin plastic film.

2. The covering of claim 1 wherein said plastic is selected from the group consisting of polyolefins, polyesters, polyvinyl florides, polyamides, polyvinyl chlorides, acrylics, acetals, polycarbonates, polystyrenes, polyurethanes, and copolymeric and terpolymeric variations of these plastics.

3. The covering of claim 1 wherein said plastic comprises a blend of plastics.

4. The covering of claim 3 wherein said blend is selected from the group consisting of polyolefins, polyesters, polyvinyl florides, polyamides, polyvinyl chlorides, acrylics, acetals, polycarbonates, polystyrenes, polyurethanes, and copolymeric and terpolymeric variations of these plastics.

5. The covering of claim 1 wherein said tackifier comprises at least one hydrocarbon resin.

6. The covering of claim 5 wherein said pressure sensitive adhesive comprises a rubbery polymer.

7. The covering of claim 6 wherein said plastic film has a rough surface, and said rough surface contacts said pressure sensitive adhesive.

8. The covering of claim 7 wherein said rough surface has from about a 40 mesh to about an 80 mesh pattern formed thereon.

9. The covering of claim 1 wherein said plastic film comprises from about 90 to about 95 weight percent plastic, and from about 5 to about 10 weight percent tackifier.

10. The covering of claim 1 wherein said plastic film comprises from about 80 to about 90 weight percent plastic, from about 1 to about 5 weight percent opaquing or coloring agent, and from about 5 to about 15 weight percent tackifier.

11. A covering for a portion of a body or an object, comprising:
a thin plastic film, said plastic film comprising from about 85 to about 95 weight percent plastic, and from about 5 to about 15 weight percent tackifier, said plastic comprising a combination of two or more polyolefins selected from the group consisting of polyethylene, LDPE, LLDPE, LMDPE, HDPE, ULDPE, mPOE, EMAC, and polypropylene; and
a pressure sensitive adhesive contacting at least a portion of, and forming a joint with, said thin plastic film.

12. The covering of claim 6 wherein said tackifier is selected from the group consisting of aliphatic resins, a copolymer of aliphatic resins, a hydrogenated or partially hydrogenated compound of aliphatic resins, and a blend of aliphatic resins.

13. The covering of claim 6 wherein said tackifier is selected from the group consisting of aromatic resins, a copolymer of aromatic resins, a hydrogenated or partially hydrogenated compound of aromatic resins, and a blend of aromatic resins.

14. The covering of claim 6 wherein said tackifier comprises a styrene polymer or copolymer.

15. The covering of claim 6 wherein said tackifier comprises an aliphatic resin and aromatic resin copolymer.

16. The covering of claim 6 wherein said tackifier comprises at least one aliphatic resin and at least one aromatic resin.

17. The covering of claim 12 wherein said tackifier comprises an aliphatic piperylene.

18. The covering of claim 1 wherein said tackifier comprises a coumarone-indene resin.

19. The covering of claim 1 wherein said tackifier comprises a polyterpene resin.

20. The covering of claim 1 wherein said tackifier comprises a styrenated terpene resin.

21. The covering of claim 6 wherein said tackifier comprises an alicyclic resin.

22. The covering of claim 6 wherein said tackifier comprises a methyl styrene polymer or copolymer.

23. The covering of claim 6 wherein said tackifier comprises a hydrogenated hydrocarbon resin.

24. The covering of claim 17 wherein said tackifier is a polymer or copolymer of 2-methyl-2-butene-piperylene.

25. The covering of claim 14 wherein said tackifier is a hydrogenated polymer or copolymer of 1-methylethenyl benzene.

26. The covering of claim 22 wherein said tackifier is a polymer or copolymer of methylstyrene-styrene.

27. The covering of claim 1 wherein said plastic comprises a blend of MPOE and EVA having a ratio by weight of about 3 to 1, respectively.

28. The covering of claim 6 wherein said pressure sensitive adhesive comprises about 40 weight percent styrene-isoprene-styrene block copolymer, about 40 weight percent hydrocarbon resin, and about 20 weight percent low molecular weight plasticizing oil.

29. A covering for a portion of a body or an object, comprising:
a thin plastic film, said plastic film comprising from about 85 to about 95 weight percent plastic, and from about 5 to about 15 weight percent tackifier, said plastic being a blend of polyolefins comprising polyethylene, mPOE, and polypropylene, and said tackifier comprises at least one hydrocarbon resin; and
a pressure sensitive adhesive contacting at least a portion of, and forming a joint with, said thin plastic film, said pressure sensitive adhesive comprising a rubbery polymer.

30. A covering for a portion of a body or an object, comprising:
a thin plastic film, said plastic film comprising from about 85 to about 95 weight percent plastic, and from about 5 to about 15 weight percent tackifier, said plastic being a blend of polyolefins comprising polyethylene, EMAC, and polypropylene, and said tackifier comprises at least one hydrocarbon resin; and
a pressure sensitive adhesive contacting at least a portion of, and forming a joint with, said thin plastic film, said pressure sensitive adhesive comprising a rubbery polymer.

31. The covering of claim 29 wherein said plastic film has a rough surface, and said rough surface contacts said pressure sensitive adhesive.

32. The covering of claim 30 wherein said plastic film has a rough surface, and said rough surface contacts said pressure sensitive adhesive.

33. The covering of claim 1 wherein said thin plastic film exhibits no significant tendency to block.

34. The covering of claim 1 wherein said covering is a body covering.

35. The body covering of claim 34 wherein said body covering is a diaper, an incontinent brief, a bandage, a medical drape, a medical gown, a medical smock, an ostomy appliance, a feminine hygiene product, a body transfer sheet, a fluid collection pouch, or an industrial clean room garment.

36. The covering of claim 1 wherein:
said covering is a diaper having a diaper tape coated with said pressure sensitive adhesive;
said thin plastic film is a diaper backsheet; and
said pressure sensitive adhesive couples said diaper tape to said diaper backsheet to form a non-refastenable joint.

37. The diaper of claim 36 wherein said diaper backsheet has a rough surface, and said rough surface contacts said pressure sensitive adhesive.

38. The covering of claim 37 wherein said rough surface is a large scale, rough surface.

39. The covering of claim 1 wherein said thin plastic film is a bandage.

40. The covering of claim 39 wherein said bandage has a rough outer surface, and, when said bandage is wrapped around an appendage of a user, said rough outer surface contacts said pressure sensitive adhesive.

41. The covering of claim 40 wherein said rough outer surface is a large scale, rough surface.

42. The covering of claim 39 wherein said bandage has an outer surface with a plurality of apertures formed thereon, and, when said bandage is wrapped around an appendage of a user, said apertured outer surface contacts said pressure sensitive adhesive.

43. The covering of claim 42 wherein said apertured outer surface is a large scale, rough surface.

44. The covering of claim 1 wherein said thin plastic film is a packaging for an object, further comprising a label, and wherein said pressure sensitive adhesive couples said label to said packaging.

45. The covering of claim 44 wherein said packaging has a rough surface, and said rough surface contacts said pressure sensitive adhesive.

46. The covering of claim 45 wherein said rough surface is a large scale, rough surface.

47. The covering of claim 44 wherein said packaging has an outer surface with a plurality of apertures formed thereon, and said apertured outer surface contacts said pressure sensitive adhesive.

48. The covering of claim 47 wherein said apertured outer surface is a large scale, rough surface.

49. The covering of claim 29 wherein said polypropylene comprises from about 7 to about 15 weight percent flexible polypropylene.

50. The covering of claim 29 wherein said polypropylene comprises from about 7 to about 15 weight percent rigid polypropylene.

51. The covering of claim 30 wherein said polypropylene comprises from about 7 to about 15 weight percent flexible polypropylene.

52. The covering of claim 30 wherein said polypropylene comprises from about 7 to about 15 weight percent rigid polypropylene.

53. The covering of claim 1 wherein said tackifier comprises a resin derived from plant byproducts.

54. The covering of claim 5 wherein said pressure sensitive adhesive comprises a polymer selected from the group consisting of styrene-butadiene-styrene block copolymers, natural rubbers, atatic polypropylenes, POEs, and EVAs.

* * * * *

UNITED STATES PATENT AND TRADEMARK OFFICE
CERTIFICATE OF CORRECTION

PATENT NO. : 6,096,420
DATED : August 1, 2000
INVENTOR(S) : Wilhoit et al.

It is certified that error appears in the above-indentified patent and that said Letters Patent is hereby corrected as shown below:

| | |
|---|---|
| Table I, Tackifier "Regal Rez 6108" | Replace "Partially Hydrogenated" With --Partially Hydrogenated Styrene-- |
| Column 3, lines 60-61 | Replace "FIGS. 1-6" With --FIGS.1-5-- |
| Column 9, line 23 | Replace "FIG. 6" With --Table 1-- |
| Column 10, line 13 | Replace "FIG.6" With --Table 1-- |
| Column 12, line 13 | Replace "MPOE" With --mPOE-- |

Signed and Sealed this

Twenty-ninth Day of May, 2001

Attest:

NICHOLAS P. GODICI

Attesting Officer     Acting Director of the United States Patent and Trademark Office